(12) United States Patent
Ehrstrom et al.

(10) Patent No.: US 12,247,264 B2
(45) Date of Patent: Mar. 11, 2025

(54) PROCESS FOR MANUFACTURING A BIMETALLIC PART USING A DILATION-CAUSING THERMAL TREATMENT

(71) Applicant: CONSTELLIUM ISSOIRE, Issoire (FR)

(72) Inventors: Jean-Christophe Ehrstrom, Grenoble (FR); Julien Laye, La Sure en Chartreuse (FR); Sylvie Arsene, Apprieu (FR); Timothy Warner, Corenc (FR)

(73) Assignee: CONSTELLIUM ISSOIRE, Issoire (FR)

(*) Notice: Subject to any disclaimer, the term of this patent is extended or adjusted under 35 U.S.C. 154(b) by 1065 days.

(21) Appl. No.: 16/973,111

(22) PCT Filed: Jun. 27, 2019

(86) PCT No.: PCT/FR2019/051597
§ 371 (c)(1),
(2) Date: Dec. 8, 2020

(87) PCT Pub. No.: WO2020/008129
PCT Pub. Date: Jan. 9, 2020

(65) Prior Publication Data
US 2021/0238706 A1    Aug. 5, 2021

(30) Foreign Application Priority Data
Jul. 3, 2018 (FR) ........................................ 1856132

(51) Int. Cl.
*C21D 9/50* (2006.01)
*B23K 20/233* (2006.01)
(Continued)

(52) U.S. Cl.
CPC .......... *C21D 9/505* (2013.01); *B23K 20/2336* (2013.01); *G16C 60/00* (2019.02); *B23K 2101/006* (2018.08); *B23K 2103/10* (2018.08)

(58) Field of Classification Search
None
See application file for complete search history.

(56) References Cited

U.S. PATENT DOCUMENTS

| 2003/0116608 A1 | 6/2003 | Litwinski |
| 2006/0054666 A1* | 3/2006 | Ehrstrom .................. B64C 3/18 228/262.51 |
| 2015/0030381 A1 | 1/2015 | Gregg et al. |

FOREIGN PATENT DOCUMENTS

| WO | 98/58759 | 12/1998 | |
| WO | WO-2005106050 A1 * | 11/2005 | ............... C21D 1/30 |
| WO | 2007/068943 A1 | 6/2007 | |

OTHER PUBLICATIONS

ASM Ready Refernce, "Thermal Properties of Metals", ASM International, pp. 9-61. (Year: 2002).*

(Continued)

*Primary Examiner* — George Wyszomierski
*Assistant Examiner* — Janell C Morillo
(74) *Attorney, Agent, or Firm* — Ladas & Parry LLP; Malcolm J. MacDonald, Esq.

(57) ABSTRACT

A process for manufacturing a bimetallic part by means of a first component formed by a first aluminum alloy and a second component formed by a second aluminum alloy, said process involving: assembling the first component and the second component to obtain an assembled part; applying a thermal treatment to the assembled part at a temperature of 100 to 250° C., the thermal treatment causing the assembled part to deform, in particular as a result of a metallurgical deformation by a precipitation of hardening phases of the first component and/or the second component; cooling the (Continued)

part to ambient temperature, upon which the part remains deformed. The process involves, prior to the assembling step, an estimation of the degree of deformation that the assembled part will undergo under the effect of the thermal treatment.

16 Claims, 6 Drawing Sheets

(51) Int. Cl.
*G16C 60/00* (2019.01)
*B23K 101/00* (2006.01)
*B23K 103/10* (2006.01)

(56) References Cited

OTHER PUBLICATIONS

International Search Report, dated Dec. 19, 2019, corresponding to International Application No. PCT/FR2019/051597.

* cited by examiner

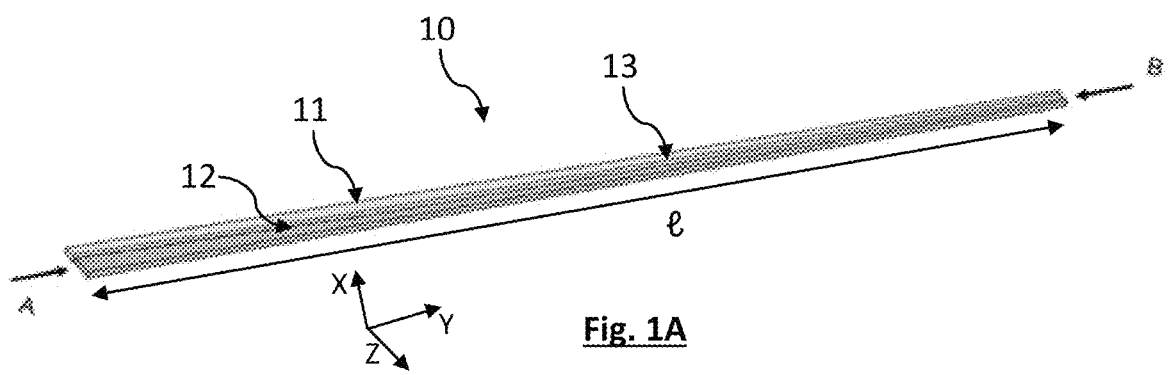
Fig. 1A
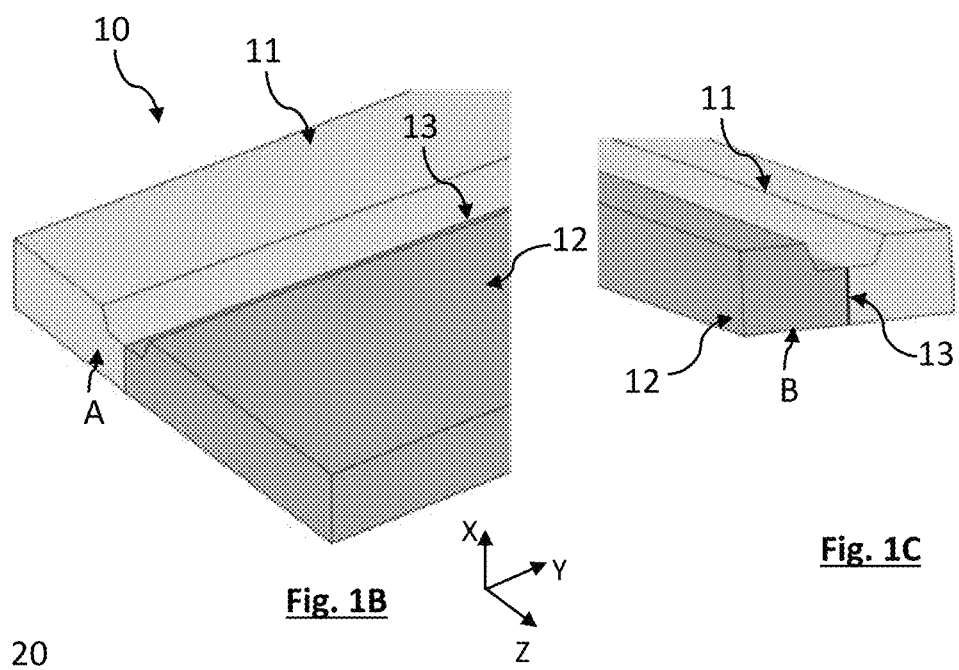
Fig. 1B
Fig. 1C
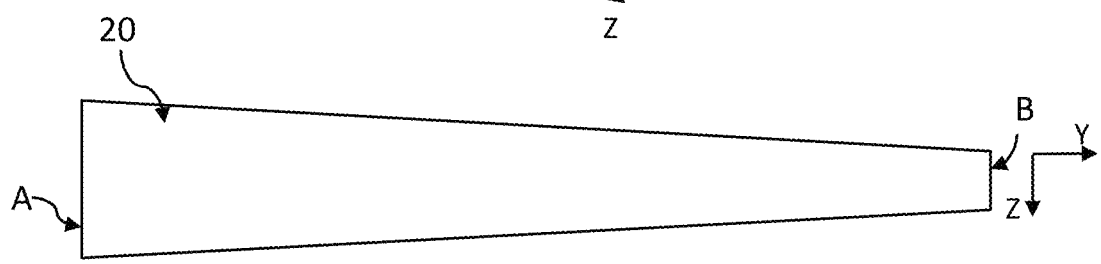
Fig. 1D
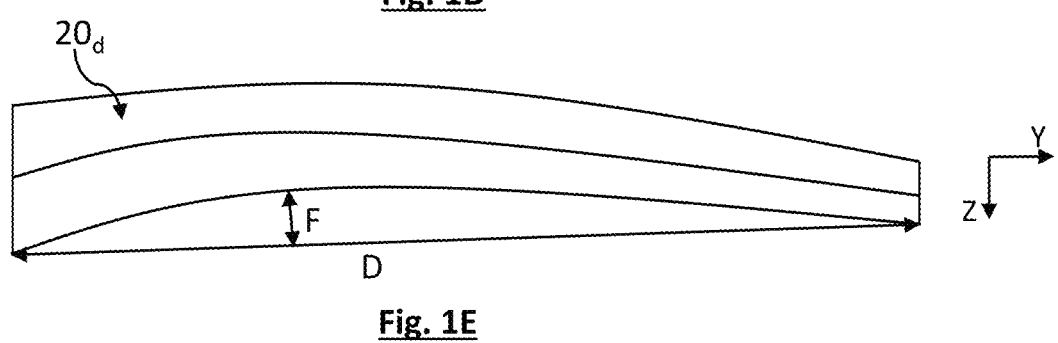
Fig. 1E

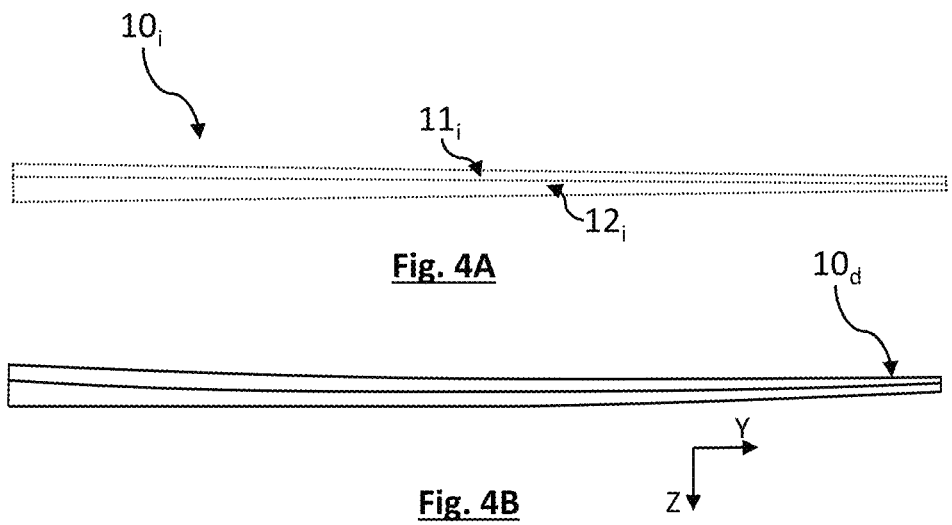
Fig. 4A
Fig. 4B
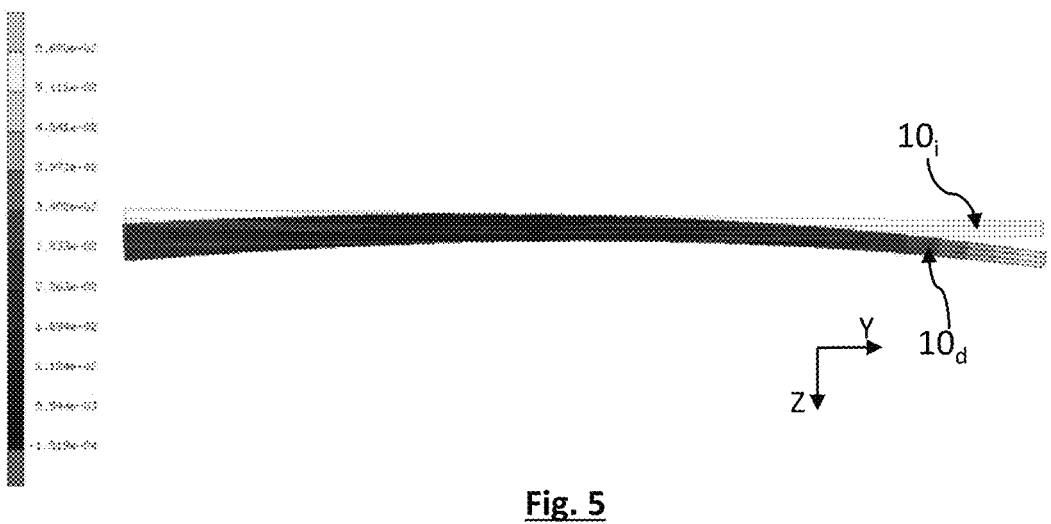
Fig. 5

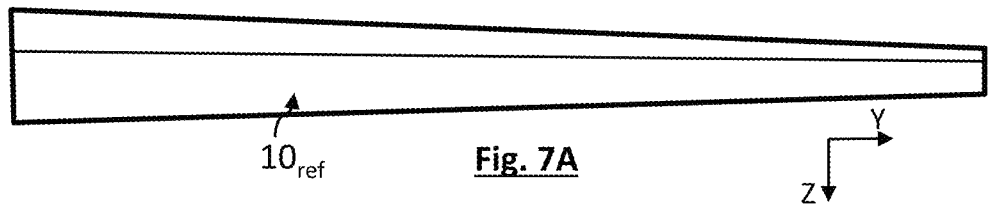
Fig. 7A
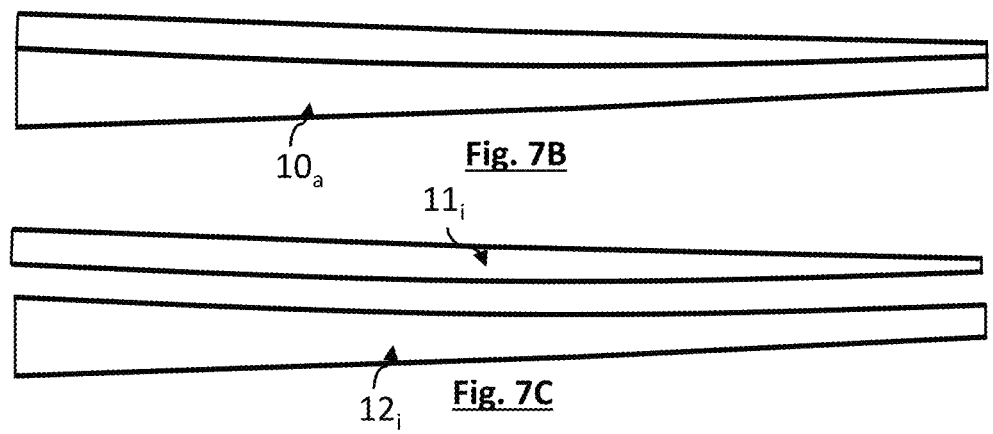
Fig. 7B
Fig. 7C
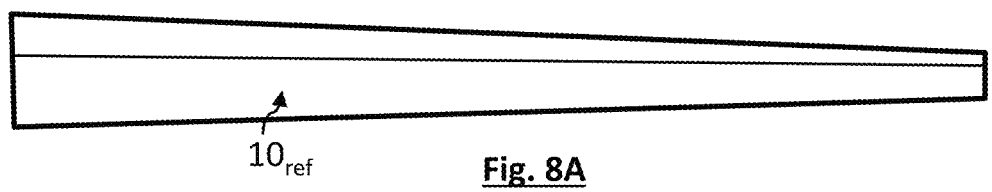
Fig. 8A
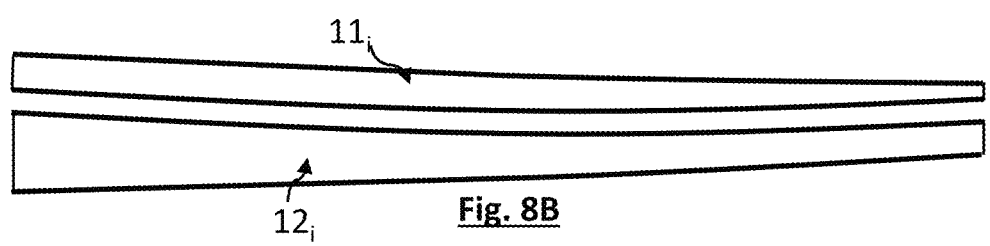
Fig. 8B

PROCESS FOR MANUFACTURING A BIMETALLIC PART USING A DILATION-CAUSING THERMAL TREATMENT

TECHNICAL FIELD

The technical field of the invention is a method for manufacturing a part, in particular a structure element, including two components connected to each other. The manufacture uses a heat treatment causing a deformation of a component or of the two components. The method makes it possible to take this deformation caused into account so as to obtain a part the form of which corresponds to a reference form.

PRIOR ART

Aluminium is a material frequently used in aeronautical construction, in particular in fuselage or wing elements, for example in the form of panels or spars. Manufacture of an aircraft wing supposes the use of panels disposed at the top part of the wing (the upper skin), as well as panels disposed at the bottom part of the wing (the lower skin). The top and bottom panels are respectively exposed to different stresses: the top panels must have good static mechanical strength, so as to be able to withstand a high compressive stress. The bottom panels must have high tolerance to damage, so as to be able to be exposed to tensile stresses.

In a wing, the bottom panels and the top panels are connected, among other things, by spars.

These must be optimised so that a top part of the spar, connected to the upper skin, has high compressive mechanical strength, while a bottom part of the spar, connected to the lower skin, has high tolerance to damage.

The document WO 2007068943 describes a method for manufacturing a structure element.

The document WO 9858759 describes a method for manufacturing by friction stir welding.

The document EP 1799391 describes a manufacturing method making it possible to obtain a structure element, for example a spar, obtained by welding two different aluminium alloys, and having respectively high compressive mechanical strength and high tolerance to damage.

The welding of the two alloys can in particular be carried out by friction stir welding. Friction stir welding makes it possible in fact to perform an assembly of alloys that cannot be welded by fusion welding methods, during which the parts to be welded are in the liquid phase. Thus, during friction stir welding, the parts to be welded are in the solid phase. It makes it possible for example to assemble alloys of the 2XXX and 7XXX type. It is known that alloys of the 2XXX type are adapted to the specifications for the lower skins, while the alloys of the 7XXX type are adapted to the specifications for the upper skins. The welding thereof makes it possible to obtain a structure element having optimum characteristics for connecting a lower skin and an upper skin.

According to the document cited above, post-welding ageing is carried out, so as to improve certain mechanical properties, for example corrosion resistance.

The inventors of the invention described below propose an improvement to the method described above, in particular for producing very long parts, exceeding 5 metres or even 10 or metres.

DESCRIPTION OF THE INVENTION

A first object of the invention is a method for manufacturing a bimetallic part, using a first component formed by a first aluminium alloy and a second component formed by a second aluminium alloy, the first and second aluminium alloys being different from each other, the first component and the second component extending:
along a longitudinal axis, over a length greater than 5 metres;
and along a lateral axis perpendicular to the longitudinal axis, over a width greater than one tenth of the length;
the method including the following steps:
assembling the first component against the second component along the longitudinal axis, so as to obtain an assembled part;
applying a heat treatment to the assembled part, at a temperature of between 100° C. and 250° C., the heat treatment causing a deformation of the assembled part, referred to as induced deformation, under the effect of a change in metallurgical nature in the first aluminium alloy and/or in the second aluminium alloy;
cooling to ambient temperature, after which said induced deformation remains;
the method being characterised in that it includes, prior to the assembly,
a) determining a reference form, corresponding to a form that is desired at the end of manufacture;
b) estimating the deformation of the assembled part induced by the heat treatment;
c) defining an initial form of the first component and an initial form of the second component taking into account the reference form determined during step a) and the deformation estimated during step b), so that, at the end of the heat treatment, the part extends in the reference form;
d) obtaining the first component and the second component according to the respective initial forms thereof defined during step c).

The heat treatment may in particular be an ageing. The assembly may be carried out by welding.

Change in metallurgical nature of an alloy means for example a recrystallisation or a solution heat treatment or a precipitation of alloy elements, which persists at the end of the heat treatment, in particular when the alloy returns to ambient temperature. It may in particular be a precipitation of hardening phases, this causing a deformation of the component, formed by the alloy, relating to the change of the alloy elements from the solid solution to the hardening precipitates.

In step b), the estimation of the deformation of the assembled part may in particular be done by digital modelling. Step b) can then include the following substeps:
bi) Allocating a first virtual thermal expansion coefficient to the first alloy and a second virtual thermal expansion coefficient to the second alloy and defining a virtual temperature change over time;
bii) Taking into account the first and second virtual thermal expansion coefficients and the virtual temperature change over time, and modelling the deformation of the assembled part under the effect of the heat treatment.

The virtual temperature change over time defined during substep bi) may in particular be different from a variation in temperature to which the assembled part is subjected during the heat treatment. The virtual temperature change may range between a minimum temperature and a maximum temperature, the amplitude between the minimum temperature and the maximum temperature being different from a variation in temperature to which the assembled part is subjected during the heat treatment.

In substep bi), the first virtual thermal expansion coefficient and the second virtual thermal expansion coefficient, as well as the virtual temperature change, can be defined experimentally. According to one embodiment, the first and second virtual thermal expansion coefficients and the virtual temperature change can be defined by:

applying the heat treatment to a test piece, representative of the assembled part, in order to obtain an experimental induced deformation;

digitally modelling the test piece, in order to obtain a modelled deformation, the modelling taking into account the first virtual thermal expansion coefficient, the second virtual thermal expansion coefficient and the virtual temperature change;

adjusting the first virtual thermal expansion coefficient, the second virtual thermal expansion coefficient and the virtual temperature change so that the modelled deformation corresponds to the deformation of the test piece.

According to another embodiment, the first virtual thermal expansion coefficient, the second virtual expansion coefficient and the virtual temperature change can be defined using a measurement, by dilatometry, of the metallurgical deformation, corresponding to the dimensional difference in each component between start and end of the heat treatment. The measurements are then made on test pieces, each test piece being respectively representative of the first component and the second component. The difference in the virtual thermal expansion coefficients between the alloys can then be adjusted to the measurements made by dilatometry, by taking into account a virtual temperature change.

In step b), the modelling takes into account the elastic behaviour of the two alloys. It can take into account the different Young's moduli for each alloy.

According to one embodiment, the first alloy is a type 2XXX aluminium alloy and the second alloy is a type 7XXX aluminium alloy. When the heat treatment is an ageing, the first virtual thermal expansion coefficient may be strictly greater than the second virtual thermal expansion coefficient.

According to one embodiment, the assembly is carried out by welding and the heat treatment is an ageing. The method can then comprise a step b') of estimating a deformation of the assembled part due to the welding, in order to define an intermediate form of the assembled part, between the welding and the ageing, so that, in step c), in defining the initial form of the first component and the second component, account is taken of the reference form and the intermediate form of the assembled part. Step b') can in particular be performed by digital modelling. It can then include the following substeps:

b'i) allocating a first auxiliary virtual thermal expansion coefficient to the first alloy and a second auxiliary virtual thermal expansion coefficient to the second alloy and defining an auxiliary virtual temperature change over time;

b'ii)' taking into account the first and second auxiliary virtual thermal expansion coefficients and the auxiliary virtual temperature change over time, and modelling the deformation of the part during welding.

A second object of the invention is a part produced according to the first object of the invention extending over a length greater than 5 metres and preferably greater than 10 metres.

A third object of the invention is the use of a part according to the invention for manufacturing a component of a transport vehicle, for example a component of an aircraft, for example a spar of an aircraft wing or of a tail unit.

Other advantages and features will emerge more clearly from the following description of particular embodiments of the invention, given by way of non-limitative examples, and shown in the figures listed below.

FIGURES

FIG. 1A shows a bimetallic part, in this case a spar, to be manufactured.

FIGS. 1B and 1C show details of two opposite ends of the bimetallic part.

FIG. 1D shows a test piece. FIG. 1E shows schematically a deformation obtained experimentally by means of a so-called test piece. In this figure, the deformation is exaggerated.

Figure 2A:
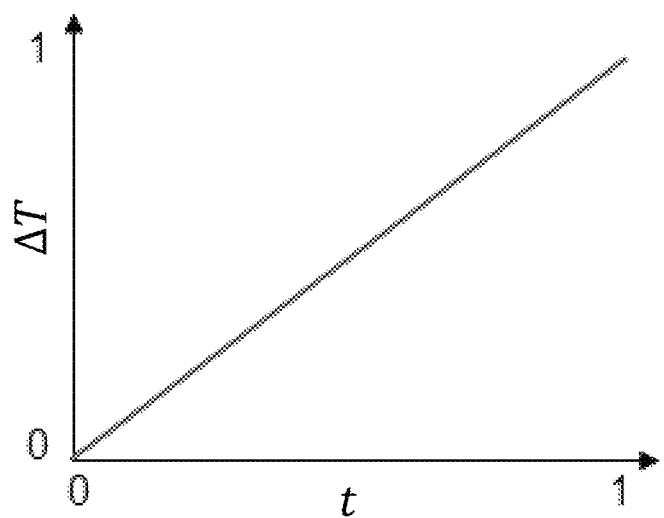
Figure 2B:
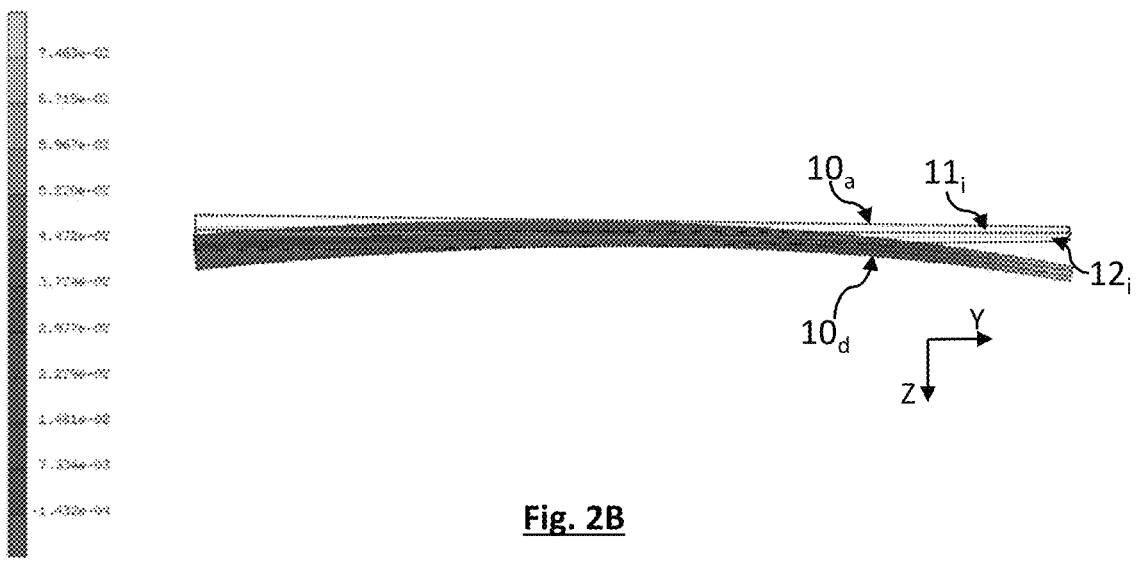

FIG. 2A shows a virtual temperature change in question for making a modelling of a deformation of a part under the effect of ageing. The X axis and Y axis represent respectively temperature and time. FIG. 2B shows a modelling of a deformation of a part under the effect of ageing.

Figures 3A, 3B:
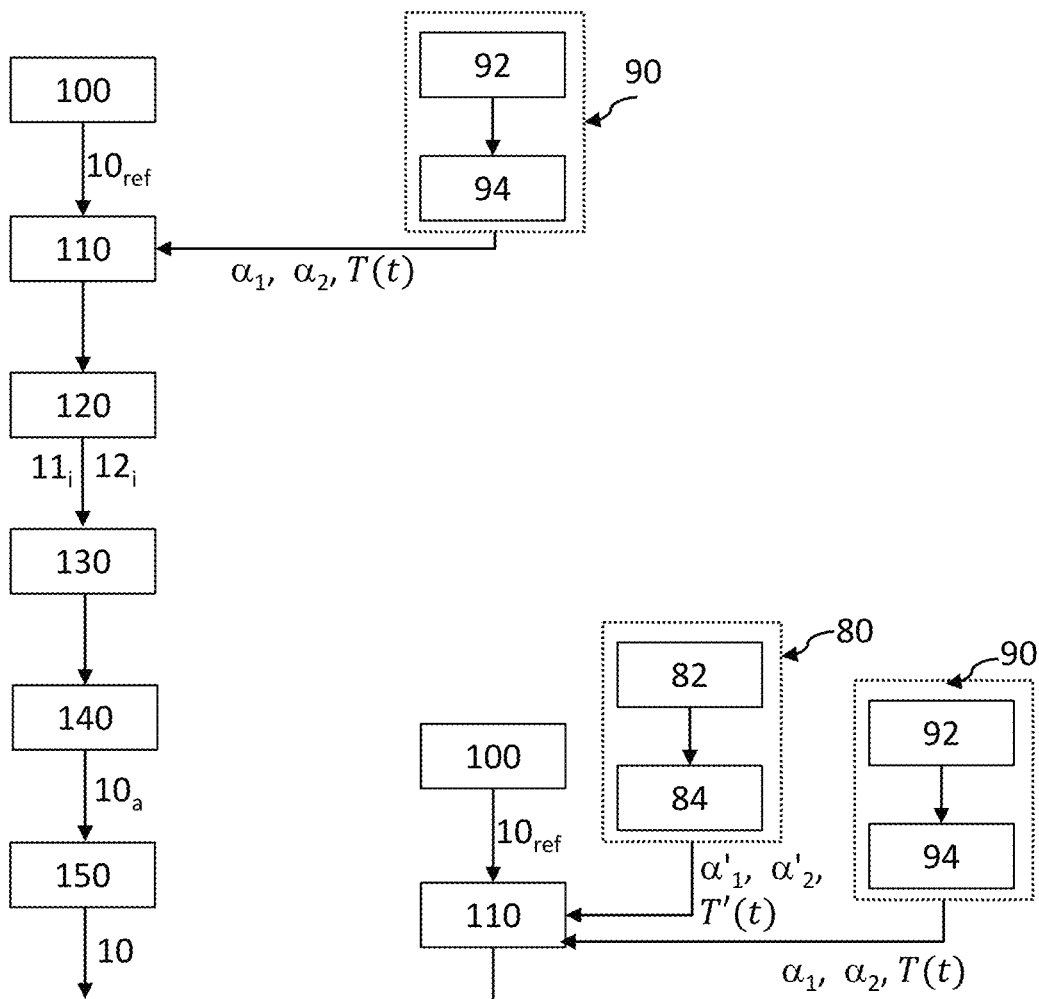

FIGS. 3A and 3B show the main steps of a method respectively according to a first embodiment and according to a second embodiment.

FIGS. 4A and 4B show a modelling of a deformation due to welding.

FIG. 5 shows a modelling of a deformation of a part due to welding and then ageing, referred to as post-welding ageing.

Figure 6A:
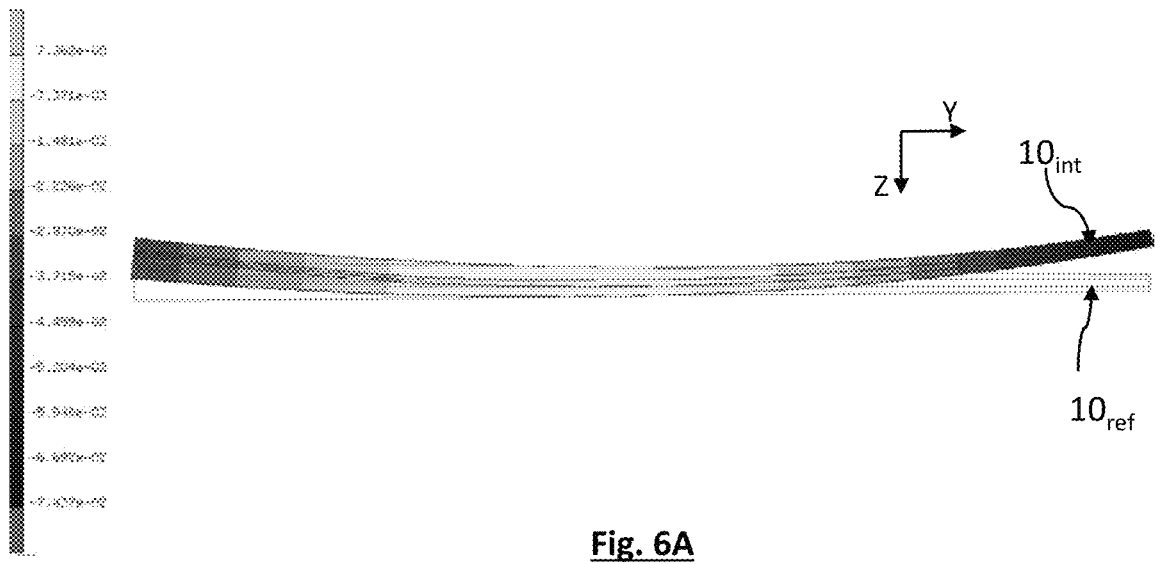
Figure 6B:

FIG. 6A shows a modelling of a so-called intermediate form, corresponding to a form of a part assembled by welding. FIG. 6B shows a modelling of a deformation due to an ageing, from the intermediate form illustrated in FIG. 6A.

FIG. 7A shows a part extending in a reference form. FIG. 7B shows a form of an assembled part, the deformation of which, following the ageing, makes it possible to obtain the reference form shown in FIG. 7A. FIG. 7C shows the two components, the assembling of which makes it possible to obtain the assembled part shown in FIG. 7B.

FIG. 8A shows a part extending in a reference form, similar to that shown in FIG. 7A. FIG. 8B shows the two components which, after welding and ageing, make it possible to obtain the part shown in FIG. 8A.

In FIGS. 3A, 4, 5, 6A and 6B, 7A to 7C, 8A to 8B, the deformation along the axis Z is multiplied by a factor of 10 with respect to the scale applied to the axis Y.

DISCLOSURE OF PARTICULAR EMBODIMENTS

Unless provided otherwise, the designations of the alloys correspond to the designations established by the Aluminium Association.

Structure element means an element constituting the structure of an item of equipment. In this application, a structure element designates particularly a member intended for example for an aircraft wing, for a fuselage or any element of a construction, in particular an aeronautical construction.

FIG. 1A shows schematically a spar 10 including a first component 11, produced in a first aluminium alloy M1, and a second component 12 produced in a second aluminium alloy M2. The first aluminium alloy M1 may for example be an alloy of the 2XXX type, while the second aluminium alloy M2 may be an alloy of the 7XXX type. The first component 11 and the second component 12 are arranged one against the other along an interface 13 of length l, along a longitudinal axis Y. The invention relates mainly to a part fabricated by assembling two components, of different materials, connected to each other along a great length. The length of the interface 13 is typically greater than 5 m or 10 m. It lies for example between 5 m and 20 m. The spar 10 extends, along the longitudinal axis Y, between two ends A and B, the respective details of which are illustrated in FIGS. 1B and 1C. The width of the part 10, along the lateral axis Z, varies, between the end A and the end B, respectively between approximately 500 mm and 800 mm and between 150 mm and 400 mm. The thickness of the part, along the transverse axis X, is for example between 50 mm and 150 mm. The plane defined by the axes X and Y is a principal plane $P_{YZ}$.

According to the manufacturing methods of the prior art, the first component 11 is connected to the second component 12 by welding. As indicated in relation to the prior art, friction stir welding is particularly suited to the production of welds of aluminium alloys that are not weldable by fusion welding methods. Friction stir welding is carried out along the interface 13. After welding, the spar 10 is subjected to ageing, referred to as post-welding ageing, so as to improve certain properties, in particular corrosion resistance and/or mechanical strength. The ageing may have the following parameters: rise to 155° C. at 30° C. per hour followed by maintenance at 155° C. for 18 hours.

The inventors have found that welding causes a deformation of the spar 10. They have also found, more unexpectedly, that post-welding ageing also causes a significant deformation of the spar 10, resulting in the appearance of curvature in the principal plane $P_{YZ}$. During post-welding ageing, two deformation phenomena occur, leading to the induced deformation of the assembled part:
- a thermal expansion that is reversible, in that it is no longer observed when returning to ambient temperature, at the end of the ageing;
- metallurgical deformation due to changes of a metallurgical nature, such as the introduction and relaxation of stress, recrystallisation or solution heat treatment or precipitation of alloy elements. Unlike thermal expansion, metallurgical deformation persists when returning to ambient temperature. Metallurgical deformation may cause expansion or contraction, according to the metallurgical phenomena involved.

For example, precipitation of hardening phases causes deformation essentially attributed to the change in volume related to the change of the alloy elements of the solid solution to the hardening precipitates. If such deformation is scarcely perceptible when the part to be manufactured is short, for example around one metre, the corresponding dimensional change may become significant when the length increases, and exceeds for example 5 or 10 metres.

After the heat treatment applied to the assembled part the induced deformation of the latter is due in particular to the metallurgical deformation, as previously described, affecting each component. It is also necessary to take into account the stresses related to the fact that the two components are connected to each other. Because of the assembly, the deformation of the first component is influenced by the elasticity of the second component, and vice versa.

Experimental tests have shown that, when the first alloy M1 is an alloy of the 2050 type and the second alloy M2 is an alloy of the 7140 type, the interface length being 16 m, the deformation of the part, because of the ageing, causes a curvature defining a deflection F of 59 mm. FIG. 1D shows schematically a test piece 20, being, before the ageing, in a rectilinear form as shown in FIG. 1A. FIG. 1E shows the test piece $20_d$ after deformation, in the principal plane $P_{YZ}$, due to the ageing.

As illustrated in FIG. 1E, the deflection F corresponds to a maximum distance between the part in question, in this case the test piece $20_d$, and a straight line D connecting the ends thereof.

Thus, when welding of the two components is carried out extending over a great length, typically greater than 5 or 10 metres, and ageing is carried out on the part $10_a$ thus assembled, a part is obtained the form of which is substantially different from the form of the assembled part $10_a$, before the ageing.

There does not at the present time exist any calculation code making it possible to simulate such deformation. This stems from the fact that it is difficult to precisely simulate an expansion of a component due to precipitation in an alloy during ageing. The inventors sought to model the deformation caused by the ageing by establishing a deformation model mod.

The modelling proposed by the inventors consists of attributing a first virtual thermal expansion coefficient $\alpha_1$ to the first alloy M1, and a second virtual thermal expansion coefficient $\alpha_2$ of the second alloy M2. In the example in question, the second virtual thermal expansion coefficient $\alpha_2$ is considered to be zero. In this way, the induced deformation of the assembled part $10_a$, under the effect of the ageing, is attributed to the difference in metallurgical deformation between the component 11 of the alloy M1 and the component 12 of the alloy M2 and to the elastic deformations caused by the fact that the components are not free to expand freely since they are assembled.

According to the model mod proposed by the inventors, the ageing is assimilated to a simple change in temperature T(t) as a function of time t. It may be a case in particular of a continuous change in temperature, for example linear. The change in temperature T(t) is defined virtually, for modelling purposes, and does not correspond to the actual variation in the temperature during the ageing. It is designated by the term "virtual temperature change". The model mod aims to simulate the deformation of the assembled part $10_a$ by taking into account a simple expansion model solely based on an isotropic thermal expansion of an alloy forming one of the components of the part.

The model mod proposed by the inventors takes into account the mechanical properties of the alloys M1 and M2, for example the Young's moduli as well as the Poisson's ratios. The modelling may be carried out by finite-element computing software, for example the MARC simulation software sold by the publisher MSC. This makes it possible to estimate a thermomechanical deformation of each component under the effect of the virtual temperature change T(t).

One objective of the model mod is to provide, simply, the deformation undergone by the assembled part $10_a$ during the ageing. From the form of the assembled part $10_a$, the deformation caused by the ageing is modelled, so as to obtain a modelling of the deformed part $10_d$. The objective of the modelling is to be able to define a form of the assembled part $10_a$, before the ageing, so that, after the ageing, the part extends in a reference form $10_{cef}$. The reference form corresponds to the form that it is desired for the part 10 after ageing.

One important aspect is the parameterising of the model mod, and in particular the determination of the virtual thermal expansion coefficients $\alpha_1$ and $\alpha_2$ of the aluminium alloys M1 and M2, as well as the definition of the virtual temperature change T(t). These parameters are determined experimentally, based on tests performed on a test piece 20 or on a measurement of the expansion observed for each of the alloys between two measurements at the same temperature. When a test piece 20 is used, this preferably has a size and/or composition identical to the assembled part $10_a$. It is not essential for the test piece 20 to be strictly identical to the assembled part $10_a$. However, the composition of the test piece 20 must be sufficiently representative of that of the assembled part $10_a$, so as to be able to allow a sufficiently precise modelling of the deformation resulting from the ageing. The test carried out on the test piece 20 makes it possible to obtain a deformation $20_d$ determined experimentally, as shown schematically in FIGS. 1D and 1E. From the deformation observed, it is possible to define the parameters of the model mod, in this case $\alpha_1$, $\alpha_2$ and T(t).

Some parameters of the model mod may be fixed a priori, according to the knowledge available on the behaviour of metal alloys. For example, when the first alloy M1 is of the 2050 type and the second alloy M2 is of the 7140 type, it has been found that it could a priori be considered that $\alpha_2=0$.

One particularity of the invention is that the virtual temperature change T(t) taken into account by the model does not necessarily correspond to the variation in temperature governing the ageing. The virtual temperature change T(t) is defined arbitrarily, on the basis of the deformation observed experimentally, so as to allow a correct modelling of deformation. In the following examples, the virtual temperature change T(t) is an increasing linear function. Being based on a virtual temperature change, that is to say without correlation with the ageing performed on the part, makes it possible to obtain a simple modelling, based solely on a thermal expansion model, making it possible to obtain a realistic simulation of the thermomechanical deformation of the assembled part.

With regard to the virtual thermal expansion coefficients $\alpha_1$, $\alpha_2$ respectively allocated to the first alloy M1 and to the second alloy M2, these are determined so as to allow a correct estimation of the experimental deformation, having regard to the virtual temperature change T(t) taken into account in the model.

According to an example embodiment, a virtual temperature change T(t) is defined a priori, and then virtual thermal expansion coefficients $\alpha_1$, $\alpha_2$ making it possible to correctly model the experimental deformation observed on the test piece 20 are allocated respectively to the first and second alloys.

When the parameters of the model mod are fixed, it is possible to model the deformation so as to define a form of the assembled part $10_a$ making it possible to obtain, following the ageing, the reference form $10_{ref}$.

According to a first example, a test piece 20, similar to the piece shown in FIGS. 1A to 1C, is subjected to an ageing. An experimental deformation $20_d$ of the piece is observed, on the basis of which the parameters of the model mod are determined.

According to another example, the parameters of the model mod can be determined on the basis of measurements by dilatometry made on samples. In this case, the first virtual thermal expansion coefficient and the second virtual thermal expansion coefficient are determined according to a difference between the expansions measured. Each sample is representative either of the first alloy or of the second alloy. On the basis of such measurements, a zero virtual thermal expansion coefficient $\alpha_2$ is allocated to the second alloy, in this case the 7140 alloy. A linear increasing change in virtual temperature T(t) was defined as shown in FIG. 2A. This change represents a gradual increase of 1° C. during the ageing period. In FIG. 2A, the X axis represents the time t, the coordinate t=1 corresponding to the end of the ageing. The Y axis represents the variation in temperature, in degrees Celsius, as from an initial temperature. The virtual thermal expansion coefficient $\alpha_1$ of the first alloy (2050 alloy) was determined experimentally by dilatometry. In this example, $\alpha_1=0.05\%/°$ C.

It will be noted that the virtual temperature change T(t) taken into account in the model extends between a minimum temperature $T_{min}$ and a maximum temperature $T_{max}$. The temperature difference $T_{max}-T_{min}$ is 1° C. It is therefore different from the temperature variation $\Delta T$ caused during the ageing. The change in virtual temperature T(t) taken into account in the model is not aimed at representing the actual variations in temperature during the ageing. It just makes it possible to model the deformation due to the ageing, on the assumption that the deformation is solely due to a thermal expansion effect.

The model mod thus produced is applied to a modelled part $10_a$, shown in broken lines in FIG. 2B. A modelling of a deformed part $10_d$, has been obtained, shown schematically in grey levels in FIG. 2B. The grey-level scale corresponds to the deformation measured along the lateral axis Z. According to the model, a deflection 56 mm high is obtained, the value measured experimentally amounting to 59 mm. The consistency between the deflection values obtained by the model and by experiment attests to the quality of the modelling conferred by the model.

Having defined the deformation model mod, it is then possible to obtain an initial form $11_i$, $12_i$ of the first and second components making it possible, after assembly, to obtain an assembled part $10_a$, the form of which, after ageing, corresponds to the reference form $10_{ref}$ determined a priori.

FIG. 3A summarises the main steps of a method for manufacturing a part according to the invention:

Step 100: Determining a reference form $10_{ref}$ that is desired at the end of the assembly of the two components 11 and 12 and the heat treatment applied to the assembled part $10_a$;

Step 110: Applying a deformation model mod, so as to estimate by iteration the deformation of the part $10_a$ formed by assembling the first component 11 and the second component 12, which will give the part $10_{ref}$ after ageing. The deformation model mod is in particular a digital deformation model, as previously mentioned and described in the following examples. It can in particular be used by means of a computer.

Step 120: According to the deformation estimated during step 110, defining a first initial form $11_i$ of the first component 11 and a second initial form $12_i$ of the second component 12.

Step 130: Obtaining the first component 11 according to the first initial form $11_i$ and obtaining the second component 12 according to the second initial form $12_i$.

Step 140: Assembling the first component against the second component, so as to obtain an assembled part $10_a$. The assembly can be obtained by welding, or by adhesive bonding or clamping of the first component 11 and second component 12.

Step 150: Applying the ageing to the assembled part $10_a$, so that, at the end of the ageing, the fabricated part 10 deforms in order to obtain the reference form $10_{ref}$.

Step 110 requires recourse to a modelling of the part deformed during the ageing. Such a modelling supposes the prior establishment of the deformation model mod, which is the object of a step 90. The step 90 includes two substeps:

Substep 92: Making measurements by dilatometry on specimens, each specimen representing the first alloy and the second alloy. Alternatively, substep 92 may include an observation of an experimental deformation of a test piece, as previously described.

Substep 94: From the measurements resulting from substep 92, defining the parameters of a thermomechanical deformation model. As previously described, the parameters are the virtual thermal expansion coefficients $\alpha_1$ and $\alpha_2$ and the virtual temperature change T(t).

According to one embodiment, described in relation to FIG. 3B, the assembly itself causes a deformation of the first component 11 and/or of the second component 12, for example by expansion. The method can then take into account the deformation during assembly. This is in particular the case when the assembly is a welding. It is then possible to model the deformation during assembly by a deformation model $mod_{aux}$, referred to as an auxiliary deformation model.

In this case, the step 110 also includes estimating the deformation of the first component 11 and the second component 12 during the assembly. During step 120, the following are then defined:
- from the reference form $10_{ref}$, a form, referred to as the intermediate form, $10_{int}$, of the assembled part $10_a$, taking into account the deformation due to the ageing, by the deformation model mod;
- from the intermediate form $10_{int}$, the initial form 11; of the first component and the initial form 12; of the second component, taking into account the auxiliary deformation model $mod_{aux}$, relating to the welding, from the intermediate form $10_{int}$.

In this case, step 110 requires recourse to a modelling of the part deformed during the welding. Such modelling supposes the prior establishment of the auxiliary deformation model $mod_{aux}$, which is the object of step 80. Establishment of the auxiliary deformation model includes two substeps:

Substep 82: Applying the welding to a test piece, representative of the part to be manufactured 10, and obtaining of an experimental deformation.

Substep 84: From the experimental deformation, defining the parameters of the auxiliary deformation model. As described hereinafter, the parameters are auxiliary virtual thermal expansion coefficients $\alpha'_1$ and $\alpha'_2$ and an auxiliary virtual temperature change T'(t).

The establishment of an auxiliary deformation model $mod_{aux}$, is described below in relation to FIG. 4.

The auxiliary deformation model $mod_{aux}$ is similar to the deformation model corresponding to the ageing: it takes into account:
- a virtual temperature change, referred to as auxiliary virtual temperature change T'(t);
- a first auxiliary virtual thermal expansion coefficient $\alpha'_1$ attributed to the first component 11;
- a second auxiliary virtual thermal expansion coefficient $\alpha'_2$ attributed to the second component 12.

The parameters of the auxiliary model $mod_{aux}$, that is to say the auxiliary virtual thermal expansion coefficients $\alpha'_1$ and $\alpha'_2$ and the auxiliary virtual temperature change T'(t), are adjusted according to an experimental test representing a welding operation. As indicated in relation to step 80, the experimental test is carried out using a test piece. During the welding, the components forming the test piece deform and the deformation thereof is characterised. Next the parameters of the auxiliary deformation model $mod_{aux}$ are determined, allowing a correct modelling of the experimental deformation obtained.

Such an auxiliary deformation model $mod_{aux}$, was defined experimentally. The first alloy, in this case the 2050 alloy, was allocated a zero auxiliary virtual thermal expansion coefficient $\alpha'_1$. A linear and increasing temperature change T'(t) was defined, similar to the one shown in FIG. 2A, the coordinate 1 on the X axis corresponding to the end of the welding. The Y axis represents the variation in temperature, in degrees Celsius, as from an initial temperature. The auxiliary virtual thermal expansion coefficient $\alpha'_2$ of the second alloy (7140 alloy) was determined so that the modelling of the deformation of the test piece does indeed correspond to the experimental deformation observed. In this example, $\alpha'_2=0.12\%/°$ C. It will be noted that the auxiliary virtual thermal expansion coefficient respectively attributed to each alloy, during the establishment of the auxiliary deformation model $mod_{aux}$, is different from the virtual thermal expansion coefficient respectively allocated to each alloy when the deformation model mod was established.

FIGS. 4A and 4B show an example of application of an auxiliary deformation model $mod_{aux}$ to a first component 11 and to a second component 12. Before the application of the auxiliary deformation model, each component extends in an initial reference form 11i, 12; (see FIG. 4A). After the welding, a deformed part $10_d$ is obtained (see FIG. 4B). According to the auxiliary deformation model previously described, a deflection of height 13 mm is obtained, the value measured experimentally amounting to 12 mm. This shows that the auxiliary deformation model manages to correctly simulate the deformation undergone by the part during welding.

The example described in relation to FIGS. 5, 6A and 6B describe the successive application of the deformation model mod, representative of the ageing, and the auxiliary deformation model $mod_{aux}$, representative of the welding, in this case a friction stir welding. In these figures, the following were established from an initial part $10_i$,
- first of all the auxiliary deformation model $mod_{aux}$, corresponding to the welding. According to this model, the first alloy and the second alloy are respectively allocated auxiliary virtual thermal expansion coefficients $\alpha'_1=0\%/°$ C., $\alpha'_2=0.12\%/°$ C., the auxiliary virtual temperature change T'(t) being as described in FIG. 2A, the X axis t=1 designating the instant at which the welding ends;
- then the deformation model mod, corresponding to the ageing, described in relation to FIGS. 3A and 3B. According to this model, the first alloy and the second alloy are respectively allocated virtual thermal expansion coefficients $\alpha_1=0.05\%/°$ C., $\alpha_2=0.0\%/°$ C., the virtual temperature change T(t) being as described in FIG. 2A, the X axis t=1 designating the instant at which the ageing ends.

FIG. 5 shows an example of successive application of the two deformation models to a part 10, as previously described. The form depicted in grey levels corresponds to a modelling of the deformation $10_d$ following the successive application of the two deformation models mod and $mod_{aux}$. The scale of the grey levels corresponds to the deformation measured along the lateral axis Z. According to the model, a deflection of height 42 mm is obtained, the value measured experimentally amounting to 47 mm. The combination of the two models is therefore considered to faithfully represent the deformations successively undergone by the part respectively during the welding and the ageing.

Knowing the reference form $10_{cef}$, it is possible to apply the deformation model mod, so as to obtain an intermediate form $10_{inter}$. The latter corresponds to the form of the assembled part which, after ageing, makes it possible to obtain the reference form $10_{cef}$. Knowing the intermediate form $10_{inter}$, the auxiliary deformation model is then applied so as to define an initial form $10_{init}$.

FIGS. 6A and 6B show an example of successive applications of two deformation models. Before the application of the model, the part 10 extends in an initial form $10_i$ so that, after the welding and the ageing, the part 10 is in the reference form $10_{ref}$.

In FIG. 6A, the form shown in grey levels corresponds to the intermediate form $10_{int}$ following the application of the auxiliary deformation model $mod_{aux}$. FIG. 6B shows the form resulting from the application of the deformation model mod, representing the deformation of the ageing, from the intermediate form $10_{int}$ shown in FIG. 6A. The scale of the grey levels corresponds to the deformation measured along the axis Z. The deformation caused by the ageing makes it possible to obtain a part 10 which, after the heat treatment, extends in the reference form $10_{ref}$.

FIGS. 7A, 7B and 7C illustrate an example of application of the invention when the connection of the first component 11 to the second component 10 does not cause any deformation. This is typically assembly by adhesive bonding. FIG. 7A shows the reference form $10_{ref}$ to be obtained. FIG. 7B is obtained by applying the deformation model mod to the reference form $10_{ref}$, in order to define a form of the assembled part $10_a$. The assembled part is obtained by adhesive bonding of the first component 11 and the second component 12, the initial forms $11_i$ and $12_i$ of which are illustrated in FIG. 7C.

FIGS. 8A and 8B illustrate an example of application of the invention when the connection of the first component 11 to the second component 12 is accompanied by a deformation. This is typically a welding. FIG. 8A shows the reference form $10_{cef}$ to be obtained. The application of the auxiliary deformation model $mod_{aux}$ to the reference form $10_{ref}$ makes it possible to define a form of the assembled part $10_a$, referred to as the intermediate form. From the intermediate form of the assembled part, application of the auxiliary deformation model makes it possible to obtain an initial form $11_i$ of the first component and an initial form $12_i$ of the second component. The initial forms $11_i$ and $12_i$ are illustrated in FIG. 8B.

The invention can be implemented in the manufacture of parts intended to form structure elements, extending in particular along great lengths, typically greater than 5 metres or even 10 metres.

The invention claimed is:

1. A method for manufacturing a bimetallic part, comprising:
   providing a first component formed by a first aluminium alloy and a second component formed by a second aluminium alloy, the first and second aluminium alloys being different from each other, the first component and the second component extending: along a longitudinal axis, over a length greater than five meters; and along a lateral axis perpendicular to the longitudinal axis, over a width greater than one tenth of the length;
   carrying out the following steps:
   a) determining a reference form corresponding to a form that is desired at the end of manufacture;
   b) estimating the deformation of the assembled part induced by the heat treatment by digital modelling;
   c) defining an initial form of the first component and an initial form of a second component, taking into account the reference form determined during step a) and the induced deformation estimated during step b), so that, at the end of the heat treatment, the part extends in the reference form; and
   d) obtaining the first component and the second component according to the respective initial forms thereof defined during step c);
   assembling the first component against the second component along the longitudinal axis to obtain an assembled part;
   applying a heat treatment to the assembled part, at a temperature of between 100° C. and 250° C., the heat treatment causing an induced deformation of the assembled part, under the effect of a change in metallurgical nature in at least one of the first aluminium alloy and the second aluminium alloy;
   cooling to ambient temperature, after which, said induced deformation remains.

2. The method according to claim 1, wherein the heat treatment is an ageing, the change in metallurgical nature being a recrystallisation or a solution heat treatment or a precipitation of alloy elements.

3. The method according to claim 1, wherein the assembling is carried out by welding.

4. The method according to claim 1, wherein, in step b), the deformation caused by the assembled part is estimated by digital modelling.

5. The method according to claim 4, wherein step b) includes the following steps:
   bi) allocating a first virtual thermal expansion coefficient to the first alloy and a second virtual thermal expansion coefficient to the second alloy, and defining a virtual temperature change over time;
   bii) taking into account the first and second virtual thermal expansion coefficients and the auxiliary virtual temperature change over time, and modelling the deformation of the assembled part during the heat treatment.

6. The method according to claim 5, wherein the virtual temperature change defined in step bi) is different from a temperature variation to which the assembled part is subjected during the heat treatment.

7. The method according to claim 6, wherein the virtual temperature change defined in step bi) extends between a minimum temperature and a maximum temperature, the amplitude between the minimum temperature and the maximum temperature being different from the temperature variation to which the assembled part is subjected during the heat treatment.

8. The method according to claim 5, wherein, in step bi), the first virtual thermal expansion coefficient, the second virtual thermal expansion coefficient, and the virtual temperature change, are defined experimentally by:
   applying the heat treatment to a test piece, representative of the assembled part, in order to obtain an induced deformed test piece;
   digitally modelling the test piece, in order to obtain a modelled deformation, the modelling taking into account the first virtual thermal expansion coefficient, the second virtual thermal expansion coefficient, and the virtual temperature change;
   adjusting the first virtual thermal expansion coefficient, the second virtual thermal expansion coefficient, and the virtual temperature change so that the modelled deformation corresponds to the deformation of the test piece.

9. The method according to claim 5, wherein, in substep bi), the first virtual thermal expansion coefficient, the second virtual thermal expansion coefficient, and the virtual temperature change are defined experimentally from a measurement, by dilatometry, on specimens, each specimen being respectively representative of the first component and the second component.

10. The method according to claim 4, wherein, in step b), the modelling takes into account the respective Young's moduli of the first alloy and the second alloy.

11. The method according to claim 5, wherein the first alloy is an aluminium alloy of the type 2XXX, and the second alloy is an aluminium alloy of the type 7XXX.

12. The method according to claim 11, wherein the heat treatment is an ageing, and wherein the first virtual thermal expansion coefficient is strictly greater than the second virtual thermal expansion coefficient.

13. The method according to claim 1, wherein the assembly is carried out by welding, the heat treatment being an ageing.

14. The method according to claim 13, also including a step b') of estimating an expansion of at least one of the first component and of the second component during the welding, in order to define an intermediate form of the assembled part, between the welding and the ageing, so that, in step c), in defining the initial form of the first component and the second component, account is taken of the reference form and the intermediate form of the assembled part.

15. The method according to claim 14, wherein step b') is carried out by digital modelling.

16. The method according to claim 15, wherein step b') includes the following steps:
- allocating a first auxiliary virtual thermal expansion coefficient to the first alloy and a second auxiliary virtual thermal expansion coefficient to the second alloy and defining an auxiliary virtual temperature change over time;
- taking into account the first and second auxiliary virtual thermal expansion coefficients and the auxiliary virtual temperature change over time, and modelling the deformation of the part during welding.

* * * * *